(12) United States Patent
Gray

(10) Patent No.: US 6,700,032 B1
(45) Date of Patent: Mar. 2, 2004

(54) WOUND CARE MANAGEMENT

(75) Inventor: John Patrick Gray, New South Wales (AU)

(73) Assignee: Leatherite Pty Limited, New South Wales (AU)

( * ) Notice: Subject to any disclaimer, the term of this patent is extended or adjusted under 35 U.S.C. 154(b) by 0 days.

(21) Appl. No.: 09/142,094

(22) PCT Filed: Mar. 7, 1997

(86) PCT No.: PCT/AU97/00144
§ 371 (c)(1),
(2), (4) Date: Oct. 9, 1998

(87) PCT Pub. No.: WO97/32613
PCT Pub. Date: Sep. 12, 1997

(30) Foreign Application Priority Data

Mar. 7, 1996 (AU) .............................. PN 8519

(51) Int. Cl.$^7$ .............................................. A61F 13/00
(52) U.S. Cl. .............................. 602/48; 602/41; 602/42; 602/43
(58) Field of Search ................. 424/45–47; 602/41–47, 602/48

(56) References Cited

U.S. PATENT DOCUMENTS

| | | | |
|---|---|---|---|
| 4,578,066 A | * | 3/1986 | O'Connor |
| 5,098,693 A | | 3/1992 | Faas, Jr. et al. |
| 5,120,325 A | * | 6/1992 | Dow, Jr. |

FOREIGN PATENT DOCUMENTS

| | | |
|---|---|---|
| EP | 72251 | 2/1983 |
| EP | 475807 | 3/1992 |
| WO | WO93/02717 | 2/1993 |

OTHER PUBLICATIONS

Derwent Abstract Accession No. 92–398476/48–WO 92/19194 A.
Derwent Abstract Accession No. 97–126713/12–JP 09010296.
Derwent Abstract Accession No. 92–421002/51–JP 04317654.
Derwent Abstract Accession No. 92–249360/34–JP 03162853.
Derwent Abstract Accession No. 66758–JP 56092–209.

* cited by examiner

Primary Examiner—Nicholas D. Lucchesi
Assistant Examiner—Lalita M Hamilton
(74) Attorney, Agent, or Firm—Galgano & Burke

(57) ABSTRACT

The invention relates to a bandage or wound dressing fabricated from a natural or synthetic film-forming material, such as a hydrophobic polymeric membrane, incorporating a therapeutically effective amount of one or more therapeutically active (e.g. anti-microbial) compounds, including Triclosan, within the matrix thereof. The incorporation of Triclosan provides continuous inherent control of the growth of a broad range of microorganisms, which promotes better wound care management and wound healing.

27 Claims, 1 Drawing Sheet

WOUND CARE MANAGEMENT

TECHNICAL FIELD

The present invention relates to improvements in wound care management using improved anti-microbial and anti-inflammatory wound dressings.

BACKGROUND ART

It was not until the 19th century that cotton wool and gauze were commonly used to handle wounds, and cotton gauze is still often used in hospitals today as a wound dressing. The ideal wound dressing:

- Removes excess exudate from the wound, but keeps the wound moist, preventing dehydration; wound exudate is in fact a bactericide which if left in position in moderate amounts tends to speed up the healing process
- Allows gaseous exchange
- Provides thermal insulation
- Is impermeable to micro-organisms
- Has low adherence properties
- Is free from particulate and toxic contaminants.

However, the treatment of chronic wounds, ulcers and the like is a problem area where topical application of anti-microbial agents alone are ineffective in wound healing, due to a large extent to leaching of the anti-microbial agent from the wound site and the inability to be able to maintain an effective amount of the agent in contact with the wound site.

Modern fibre technology has allowed low concentrations of biocide to be incorporated into the fibres of the bandage or dressing, and in this way to prevent broad spectrum microbial growth in the target zone, and to allow the agent to remain effective over longer periods.

In recent time I have developed a product initially for veterinary applications, but which has potential for the treatment of humans, which utilises a gauze pad in an elastic bandage which is adapted to conform to the treatment site on the animal, wherein the textile material of the gauze pad incorporates the anti-microbial compound, Triclosan, within the interstitial spaces of the polymeric fibre material from which the gauze pad is fabricated.

This bandage or dressing has shown itself to be a potentially valuable product in improved wound care management, because of an unexpected apparently synergistic property of the Triclosan in this form of application, in not only preventing broad spectrum microbial growth and reducing inflammation in the target zone, but also in encouraging wound healing. However, there is room for improvement with this type of product—and especially in the area of more efficient delivery of the therapeutic agent to the wound care site and in increased therapeutically effective concentrations.

DISCLOSURE OF THE INVENTION

It is an object of the present invention to provide new or improved wound care dressings or bandages comprising therapeutically effective amounts of a therapeutic agent such as Triclosan which goes at least some way towards overcoming or at least minimising the prior art problems or limitations outlined above.

It is another object of the present invention to provide an improved form of bandage or dressing which allows for more efficient delivery of a therapeutic agent to the wound care site in increased therapeutically effective concentrations.

It is a further object of this invention to provide an improved form of bandage or dressing comprising a polymeric material (natural or synthetic) with one or more therapeutically active (e.g. anti-microbial) compounds incorporated within the polymeric matrix.

It is yet another object of the present invention to provide an improved form of bandage or dressing that incorporates a therapeutically active agent, or combination of agents useful in wound care management for the promotion of wound healing.

Additional objects and advantages of the invention will be set forth in the description which follows, and in part will be obvious from the description, or may be learned by practice of the invention.

These and other objects of the invention will become more apparent from the following description.

According to one aspect of the present invention there is provided a bandage or dressing for wound care management, comprising an outer fabric support, preferably an elastomeric fabric support, and an inner pad, wherein the inner pad includes an outer membrane surface, preferably fabricated from a film-forming material, and incorporating a therapeutically effective amount of one or more therapeutically active (e.g. anti-microbial) compounds including Triclosan in the matrix thereof. The pad may be integral with or separate from the outer fabric support. The Triclosan is ideally incorporated into the membrane matrix, but may also be incorporated into the material of the inner pad contained by the membrane.

The therapeutically active agent is held in the polymeric matrices, so that migration is inhibited, causing the controlled release of the agent.

The present invention also provides a method of making the therapeutically active bandage or dressing wherein one or more therapeutically active agents, including Triclosan, is incorporated into the device by blending the agent into the polymer resin before or during forming a film of the polymeric material.

According to another aspect of the invention, the wound dressing comprises an absorbent pad having a construction similar to that used in disposable diaper-, sanitary napkin- or incontinence clothing-construction, having a gas and/or liquid pervious body-side liner, a separate outer cover sheet (optionally liquid impervious) and an absorbent body disposed therebetween. The finer and/or the absorbent body are fabricated from materials which incorporate a therapeutically effective amount of one or more therapeutically active (e.g. anti-microbial) substances including Triclosan in the matrix or interstitial spaces thereof, to ensure that the therapeutically active substances(s) is/are in constant close proxmity to the wound site.

According to the present invention, the term "therapeutically effective amount" means an amount of therapeutic (anti-microbial) agent and/or mixture thereof which is capable of promoting wound healing and retarding or preventing microbial colonisation and adherence to the surface of the polymeric materials used herein while causing minimum undesirable side effects when in contact with living tissue.

FURTHER DESCRIPTION AND BEST MODE OF CARRYING OUT THE INVENTION

Figure 1:
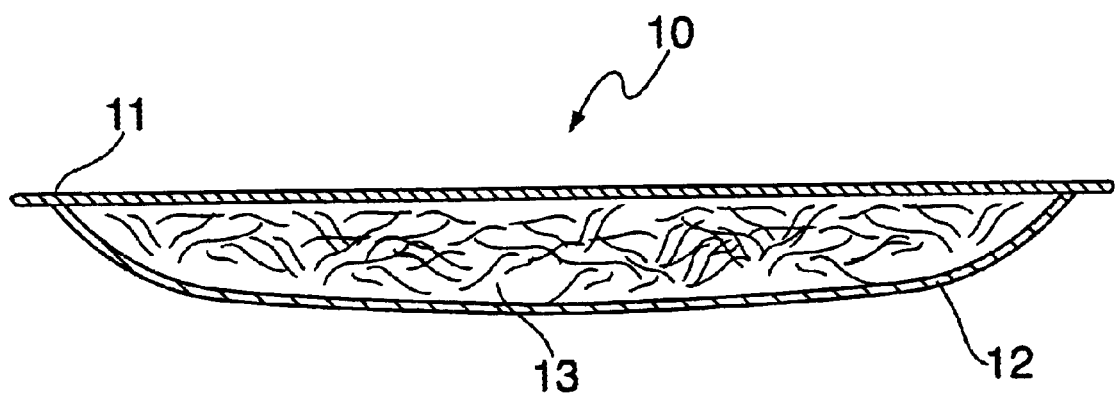
FIG. 1 shows a cross-sectional representation of a bandage or dressing for wound care management according to one embodiment of the present invention.

Referring to the drawing, FIG. 1 illustrates a basic structure of a bandage or wound care dressing pad 10 according to one embodiment of the present invention, shown in cross-section, comprising an outer liquid-impervious support layer 11, an inner liquid-pervious body-side liner 12, and an absorbent pad 13. The absorbent pad 13 and/or the body-side liner 12 are preferably fabricated from one or more polymeric materials, comprising a polymer matrix having interstitial spaces within the matrix, which incorporate a therapeutically-effective amount of one or more therapeutically-active compounds, including Triclosan, within the matrix or interstitial spaces of the polymeric material(s) from which the absorbent pad 13 and/or the body-side liner 12 are fabricated.

The inner surface or pad of the bandage is preferably fabricated from a natural or synthetic membrane or film-forming material of either organic or inorganic, animal or vegetable origin, or from plastics materials. For example, from gelatins or from vegetable gums, or from hydrophilic or hydrophobic film forming plastics materials such polyvinylchlorides polyacetates or polyamides which are cast or coated as a film or membrane in the usual way.

Suitable polymeric materials include but are not limited to silastic or other silicone-based material, polyethylene tecephtalate (PET), dacron, knitted dacron, velour dacron, polyglacin, chromic gut, nylon, silk, bovine arterial graft, polyethylene (PE), polyurethane, polyvinyl chlorides silastic elastomer, silicone rubber, PMMA [poly-(methyl methacrylate), latex, polypropylene (PP), polyofefin, cellulose, poly vinyl] alcohol (PVA), poly(hydroxyethyl methacrylate (PHEMA), poly(glycolic acid), poly(acrylonitrile) (PAN), floroethylene-cohexa-fluoropropylene (FEP), teflon (PTFE), Co—Cr alloys, copolymers thereof and mixtures thereof.

According to the invention, the simplest method of incorporating the therapeutically active compounds into the polymeric material is by direct compounding of the therapeutically active substance into the plastic resin before casting or the like.

For example, the therapeutic substance(s) are ideally dissolved in a suitable solvent and incorporated into the film forming material to be cast or knife coated as a film or membrane, whereby the therapeutic substances are incorporated in the interstitial spaces of the film matrix. The film or membrane is ideally fabricated from a hydrophobic polymer which is both liquid and gas permeable, but impervious to the passage of micro-organisms. The hydrophobicity of the film or membrane is a useful feature in that it reduces the tendency for the film or membrane to become attached to the wound site.

The preferred anti-microbial substance for inclusion in the film or membrane is Triclosan at concentrations of between about 0.1–30% by weight, more suitable from about 0.5–15% by weight, and preferably between about 1–1.5% by weight, to utilise its anti-inflammatory/anti-microbial therapeutic and wound-healing-promoting properties. Triclosan (generic name) is a well-known highly effective broad spectrum anti-microbial agent for topical applications, with a wide range of efficacy. It has the following chemical formula:

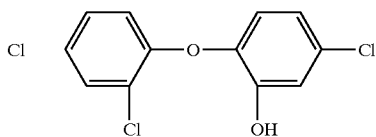

Triclosan (2,4,4'-trichloro-2'-hydroxy diphenyl ether) has the molecular formula $C_{12}H_7CL_3O_2$ and is commercially available under the trade name Irgasan (Ciba-Geigy Limited) e.g. Irgasan DP300. Its physical properties, toxicology and compatibility with various chemicals used in the hygiene area are well documented. Its uses extend from additives to soaps, deodorants and toothpastes to incorporation in textile materials and yarns. It is incorporated into clothing to control the growth of microorganisms between launderings. Other common applications include animal beds, dental floss, shoe innersoles, furniture coverings and public transport seating, to name but a few.

In the medical field it is used in the material of hospital bed sheets, surgical drapes, hospital gowns, operating gowns, and medical masks. Potential medical applications include bandages, gauze, filters and anywhere a textile or textile fibre could be used to control mould, mildew, fungus, yeast or bacterial growth.

In recent veterinary trials with woven bandages, developed by me and made from polymeric fibres incorporating Triclosan, the bandages exhibited a hitherto unexpected therapeutic, possibly synergistic, property, which essentially promotes better wound care management and wound healing. This in turn has led to the development of the present invention and the use of Triclosan-containing polymers in improved infection control and wound care management following, for example, surgical procedures.

Triclosan is readily available commercially with a purity greater than 99%. The compound exhibits marked anti-microbial properties across a wide range of bacteria, fungi, and viruses. In its usage to date, Triclosan has not induced resistance in exposed organisms. The product has been marketed for many years an anti-microbial system for preserving cosmetics and industrial products, for oral care products such as toothpaste and/or hand disinfectants. Through these uses it has undergone extensive toxicological testing and been found to be safe at recommended concentrations. Irgasan also has considerable anti-inflammatory activity. Additionally, the chemical has good environmental properties, yet is stable to hydrolysis. It is poorly soluble in water and highly soluble in many organic solvents.

The properties of Triclosan have not previously been considered to be therapeutic in nature. According to the present invention it is proposed that, by appropriate application, the chemical can be used in therapeutic situations in conjunction with bandages and wound dressings.

According to the invention, Triclosan is incorporated into the polymer material by addition of Triclosan during the mixing/polymerisation stage, whereby the Triclosan is colloidally and homogeneously suspended within the amorphous zone of the polymer. The Triclosan also acts as a plasticiser with some polymers, e.g. polyurethane. Depending on the specific polymer, the Triclosan may obviate the need to use a separate plasticiser in the polymeric material. The Triclosan softens the polymer for processing and provides a degree of elasticity in the formed membrane.

The Triclosan is introduced into the interstitial spaces of the polymer material in such a way as to not effect the physical properties of the polymer/plastics material. These spaces act as reservoir for the Triclosan from which sub-micron sized particles thereof migrate to the surface of the polymer on demand. There they become a tightly bound durable part of the surface itself. In this way Triclosan in the bandage or wound dressing provides continuous inherent control of the growth of a broad range of microorganisms, including gram-positive and gram-negative bacteria, as well as fungi, moulds, mildew and yeasts. Triclosan is also believed to exhibit some virus-inactivating properties which prevent virus replication.

Triclosan penetrates and disrupts the metabolic function of thin-walled microorganisms, interrupting their ability to function, grow and reproduce. Normal human cells are thick-walled, and are therefore unaffected by Triclosan.

In use, the continuous presence of Triclosan in the bandage or wound dressing prevents or reduces broad spectrum microbial growth and inflammatory processes in the underlying wound area and promotes ideal conditions for wound healing.

Although exemplary embodiments of the present invention have been referred to herein, it will be apparent to those having ordinary skill in the art that a number of changes, modifications or alterations to the invention described herein may be made, none of which depart from the spirit of the present invention. All such changes, modifications and alterations should therefore be seen as being within the scope of the present invention.

It should be appreciated that the present invention provides a substantial advance in anti-microbial bandages and wound care management, providing all the herein-described advantages without incurring any relative disadvantages.

What is claimed is:

1. A bandage or dressing for wound care management comprising an outer fabric support layer and an inner fluid pervious body-side liner fabricated from one or more polymeric materials comprising a polymer matrix with interstitial spaces within said matrix, and including a therapeutically effective amount of one or more therapeutically active compounds including Triclosan in the matrix or interstitial spaces of the polymeric material(s) from which said liner is fabricated.

2. A bandage or wound care dressing according to claim 1 wherein the therapeutically active compounds comprise about 0.1% to about 30% by weight of the pad.

3. A bandage or wound care dressing according to claim 1 wherein the therapeutically active compound comprises about 0.5% to about 15% by weight of the pad.

4. A bandage or wound care dressing according to claim 1 wherein the therapeutically active compound comprises about 1 and about 1.5% by weight of the pad.

5. A bandage or dressing for wound care management according to claim 1 wherein the liner comprises a synthetic polymeric material.

6. A bandage or dressing for wound care management according to claim 1 wherein the liner comprises a natural polymeric material.

7. A bandage or dressing for wound care management according to claim 1 wherein the liner comprises a polymeric material selected from silastic or other silicone-based material, polyethylene tecephtalate (PET), dacron, knitted dacron, velour dacron, polyglacin, chromic gut, nylon, silk, bovine arterial graft, polyethylene (PE), polyurethane, polyvinyl chlorides silastic elastomer, silicone rubber, PMMA [poly-(methyl methacrylate), latex, polypropylene (PP), polyofefin, cellulose, poly vinyl] alcohol (PVA), poly (hydroxyethyl Methacrylate (PHEMA), poly(glycolic acid), poly(acrylonitrile) (PAN), fluoroethylene-cohexa-fluoropropylene (FEP), teflon (PTFE), Co—Cr alloys, copolymers thereof and mixtures thereof.

8. A bandage or dressing for wound care management according to claim 1 wherein the liner comprises a polymeric material selected from silastic or other silicone-based material, polyethylene tecephtalate (PET), dacron, knitted dacron, velour dacron, polyglacin, chromic gut, nylon, silk, bovine arterial graft, polyethylene (PE), polyurethane, polyvinyl chlorides silastic elastomer, silicone rubber, PMMA [poly-(methyl methacrylate), latex, polypropylene (PP) polyolefin, cellulose, poly vinyl] alcohol (PVA), poly (hydroxyethyl Methacrylate (PHEMA), poly(glycolic acid), poly(acrylonitrile) (PAN), fluoroethylene-cohexa-fluoropropylene (FEP), teflon (PTFE), Co—Cr alloys, copolymers thereof and mixtures thereof.

9. An article comprising a bandage or dressing for wound care management, having an outer fabric support layer and an inner fluid pervious fabric body-side liner, and an absorbent body disposed therebetween, wherein the body-side liner and/or the absorbent body are fabricated from one or more polymeric materials having a polymer matrix with interstitial spaces within said matrix, and including a therapeutically effective amount of one or more therapeutically active compounds including Triclosan in the matrix or interstitial spaces of the polymeric material(s) from which the said liner and/or the said absorbent body are fabricated.

10. An article according to claim 9 wherein the said body-side liner or inner layer is fabricated from a fluid pervious membrane cast from a polymeric material, wherein said polymeric material incorporates a therapeutically effective amount of one or more therapeutically active compounds including Triclosan in the matrix or interstitial spaces of the said polymeric material(s) from which the said membrane is cast.

11. An article according to claim 10 wherein the body-side liner and/or the absorbent body comprises a synthetic polymeric material.

12. An article according to claim 10 wherein the body-side liner and/or the absorbent body comprises a natural polymeric material.

13. An article according to claim 10 wherein the body-side liner comprises a polymeric material selected from silastic or other silicone-based material, polyethylene tecephtalate (PET), dacron, knitted dacron, velour dacron, polyglacin, chromic gut, nylon, silk, bovine arterial graft, polyethylene (PE), polyurethane, polyvinyl chlorides silastic elastomer, silicone rubber, PMMA [poly-(methyl methacrylate), latex, polypropylene (PP) polyolefin, cellulose, poly vinyl] alcohol (PVA), poly(hydroxyethyl Methacrylate (PHEMA), poly(glycolic acid), poly (acrylonitrile) (PAN), fluoroethylene-cohexa-fluoropropylene (FEP), teflon (PTFE), Co—Cr alloys, copolymers thereof and mixtures thereof.

14. An article according to claim 9 wherein the therapeutically active compounds comprise between 0.1% to 30% by weight of the body-side liner and/or of the pad or absorbent body.

15. An article according to claim 14 wherein the therapeutically active compound comprises between 0.5% to 15% by weight of the body-side liner and/or the pad or absorbent body.

16. An article according to claim 14 wherein the therapeutically active compound comprises between 1 and 1.5% by weight of the body-side liner and/or the pad or absorbent body.

17. An article according to claim 9 wherein the body-side liner comprises a polymeric material selected from silastic or other silicone-based material, polyethylene tecephtalate (PET), dacron, knitted dacron, velour dacron, polyglacin, chromic gut, nylon, silk, bovine arterial graft, polyethylene (PE), polyurethane, polyvinyl chlorides silastic elastomer, silicone rubber, PMMA [poly-(methyl methacrylate), latex, polypropylene (PP) polyolefin, cellulose, poly vinyl] alcohol (PVA), poly(hydroxyethyl Methacrylate (PHEMA), poly (glycolic acid), poly(acrylonitrile) (PAN), fluoroethylene-cohexa-fluoropropylene (FEP), teflon (PTFE), Co—Cr alloys, copolymers thereof and mixtures thereof.

18. An article of manufacture comprising an absorbent pad for wound care management, having an outer liquid-impervious support layer on one side and an inner fluid pervious layer on the opposite side, and an absorbent body disposed therebetween, wherein the said inner layer and/or the said absorbent body are fabricated from one or more polymeric materials having a polymer matrix with interstitial spaces within said matrix, and including a therapeutically effective amount of one or more therapeutically active compounds including Triclosan in the matrix or interstitial spaces of the polymeric material(s) from which the said inner layer or liner, and/or the said absorbent body, are fabricated.

19. An article according to claim 18 wherein the said body-side liner or inner layer is fabricated form a fluid pervious membrane cast from a polymeric material, wherein said polymeric material incorporates a therapeutically effective amount of one or more therapeutically active compounds including Triclosan in the matrix or interstitial spaced of the said polymeric material(s) from which the said membrane is cast.

20. An article according to claim 19 wherein the body-side liner and/or the absorbent body comprises a synthetic polymeric material.

21. An article according to claim 20 wherein the body-side liner comprises a polymeric material selected from silastic or other silicone-based material, polyethylene tecephtalate (PET), dacron, knitted dacron, velour dacron, polyglacin, chromic gut, nylon, silk, bovine arterial graft, polyethylene (PE), polyurethane, polyvinyl chlorides silastic elastomer, silicone rubber, PMMA [poly-(methyl methacrylate), latex, polypropylene (PP) polyolefin, cellulose, poly vinyl] alcohol (PVA), poly(hydroxyethyl Methacrylate (PHEMA), poly(glycolic acid), poly (acrylonitrile) (PAN), fluoroethylene-cohexa-fluoropropylene (FEP), teflon (PTFE), Co—Cr alloys, copolymers thereof and mixtures thereof.

22. An article according to claim 19 wherein the body-side liner and/or the absorbent body includes a natural polymeric material.

23. An article according to claim 18 wherein the therapeutically active compounds comprise between 0.1% to 30% by weight of the body-side liner and/or of the pad or absorbent body.

24. An article according to claim 23 wherein the therapeutically active compound comprises between 0.5% to 15% by weight of the body-side liner and/or the pad or absorbent body.

25. An article according to claim 23 wherein the therapeutically active compound comprises between 1 and 1.5% by weight of the body-side liner and/or the pad or absorbent body.

26. An article according to claim 18 wherein the body-side liner comprises a (polymeric material selected from silastic or other silicone-based material, polyethylene tecephtalate (PET), dacron, knitted dacron, velour dacron, polyglacin, chromic gut, nylon, silk, bovine arterial graft, polyethylene (PE), polyurethane, polyvinyl chlorides silastic elastomer, silicone rubber, PMMA [poly-(methyl methacrylate), latex, polypropylene (PP) polyolefin, cellulose, poly vinyl] alcohol (PVA), poly(hydroxyethyl Methacrylate (PHEMA), poly(glycolic acid), poly (acrylonitrile) (PAN), fluoroethylene-cohexa-fluoropropylene (FEP), teflon (PTFE), Co—Cr alloys, copolymers thereof and mixtures thereof.

27. A method for the manufacture of a therapeutically effective bandage or wound care dressing having an outer fabric support layer and an inner fluid pervious inner layer with an absorbent body disposed therebetween and wherein the said inner layer and/or said absorbent body are fabricated from one or more polymeric materials having a polymeric matrix with interstitial spaces within the matrix incorporating one or more materials including Triclosan, which method comprises incorporating a therapeutically effective amount of one or more therapeutically active compounds including Triclosan into a mixture of the polymeric materials prior to casting or spinning of the polymeric material.

* * * * *